United States Patent [19]

Hirsenkorn et al.

[11] Patent Number: 5,272,270
[45] Date of Patent: Dec. 21, 1993

[54] PROCESS FOR THE PREPARATION OF 1-ALKYLISOQUINOLINE DERIVATIVES

[75] Inventors: Rolf Hirsenkorn, Pullach; Silvia Orlitsch, Unterhaching, both of Fed. Rep. of Germany

[73] Assignee: Consortium fur elektrochemische Industrie GmbH, Munich, Fed. Rep. of Germany

[21] Appl. No.: 744,453

[22] Filed: Aug. 12, 1991

[30] Foreign Application Priority Data

Aug. 17, 1990 [DE] Fed. Rep. of Germany ....... 4026115

[51] Int. Cl.$^5$ ............................................. C07D 217/24
[52] U.S. Cl. .................................... 546/141; 546/14; 546/90
[58] Field of Search .................... 546/141, 14, 90

[56] References Cited

U.S. PATENT DOCUMENTS

| | | | |
|---|---|---|---|
| 3,452,010 | 8/1966 | Pohlke et al. | 546/141 |
| 4,757,078 | 7/1988 | Misra | 546/141 |
| 4,843,077 | 6/1989 | Hinkle et al. | 546/141 |

FOREIGN PATENT DOCUMENTS

0214905 8/1986 European Pat. Off. .

OTHER PUBLICATIONS

S. F. Dyke et al., Tetrahedon, vol. 22, pp. 3803 et seq. (1971).
K. Yamada et al., Chem. Pharm. Bulletin, vol. 30, pp. 3197 et seq. (1982).
G. Blasko et al., The Alkaloids, Academic Press, Inc., vol. 31, pp. 1, et seq. (1987).
A. I. Meyers et al., Heterocycles, vol. 28, pp. 295, et seq. (1989).
Wei Zhang et al., Journal of American Chemical Society, vol. 112, pp. 2801 et seq. (1990).
E. N. Jacobsen et al., Journal of American Chemical Society, vol. 110, pp. 1968 et seq. (1988).
B. M. Kim et al., Tetrahedon Letters, vol. 30, pp. 655 et seq. (1989).
D. Seebach et al., Helv. Chim. Acta, vol. 70, pp. 1357 et seq. (1987).
Yun He et al., Synthetic Communications, vol. 19, pp. 3051 et seq. (1989).
Chemical Abstracts 108, No. 9, Feb. 29, 1988, "The synthesis of the isoquinoline alkaloid calycotomine", p. 711, Lenz G.
Chemical Abstracts 98, No. 9, Feb. 28, 1983, Yamada K. et al., "Studies on 1,2,3,4-tetrahydroisoquinolines", p. 665.

*Primary Examiner*—C. Warren Ivy
*Assistant Examiner*—James H. Turnipseed
*Attorney, Agent, or Firm*—Collard & Roe

[57] ABSTRACT

The invention relates to a process for the preparation of 1-alkyl-1,2,3,4-tetrahydroisoquinoline derivatives of the general formula

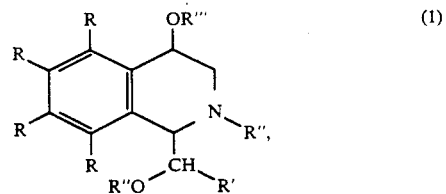

The compounds can be used for the preparation of tetrahydroisoquinolines of the reticuline type, or of the norreticuline type, by reductive removal of the OH groups or, if they carry an acyl protective group on the nitrogen, for the preparation of isoquinolines of the papaverine type by acid-catalyzed hydrolysis with removal of the acyl groups and simultaneous removal of the hydroxyl groups.

These 1-alkyl-1,2-dihydroisoquinoline derivatives can then be used for the preparation of isoquinolines of the papaverine type by aromatization by means of acids or hydrazine.

11 Claims, 1 Drawing Sheet

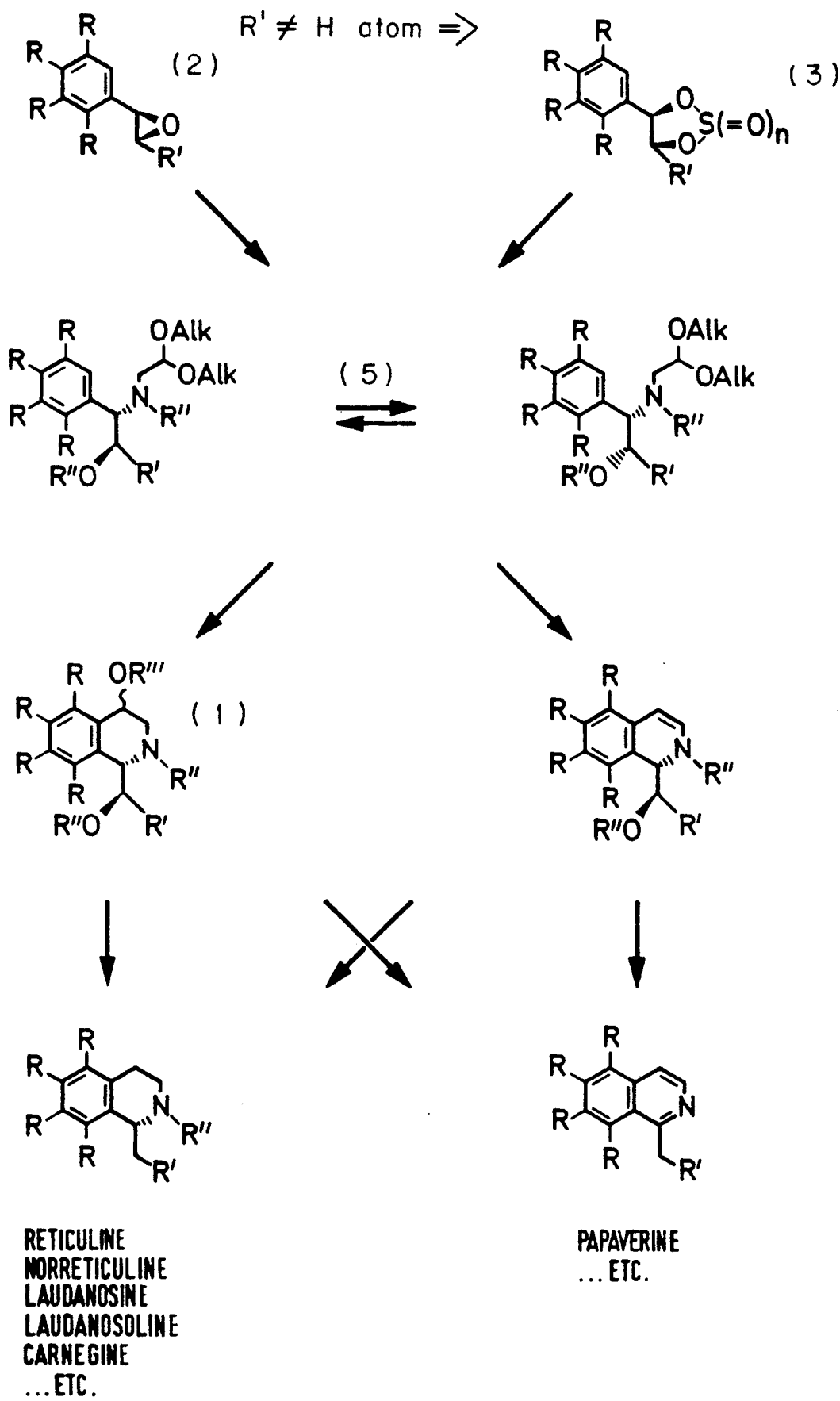

PROCESS FOR THE PREPARATION OF 1-ALKYLISOQUINOLINE DERIVATIVES

BACKGROUND OF THE INVENTION

1. Field of the Invention

The present invention relates to a process for the preparation of 1-alkylisoquinoline derivatives, in particular, 1-alkyl-1,2,3,4-tetrahydroisoquinolines and 1-alkyl-1,2-dihydroisoquinolines in which the alkyl radicals in the 1-position can also be substituted.

2. The Prior Art

The 1-alkylisoquinoline structure is the basic building block for various pharmaceutically active compounds, such as antihypertensives of the salsoline type, spasmolytics of the papaverine type or analgesics of the morphine type. Derivatives of 1-alkylisoquinoline are, therefore, useful intermediates for the preparation of active compounds of this type.

A plurality of processes are known for the preparation of 1-alkylisoquinolines in which starting either from a β-phenylethylamine and subsequent acylation of the amino group, the ring closure to the isoquinoline is carried out in the presence of acids, at elevated temperature, and known in the literature under the name "Bischler-Napieralski cyclization." 3,4-dihydroisoquinolines are formed here.

In the condensation of β-phenylethylamines with carbonyl compounds in acidic solution, the ring closure to the isoquinoline takes place by intramolecular aminomethylation, which is known in the literature as "Pictet-Spengler cyclization." 1,2,3,4-tetrahydroisoquinolines are formed here.

A third route for the preparation of isoquinoline derivatives in which aromatic aldehydes are condensed with aminoacetals, and the iminoacetals thus obtainable are then cyclized by the action of acid, which is known in the literature as "Pomeranz-Fritsch cyclization", is virtually impractical for the preparation of 1-substituted isoquinoline derivatives, such as 1-benzylisoquinoline derivatives, as the corresponding aromatic ketones are not only accessible with difficulty, but these also react with aminoacetals only with difficulty, or not at all. Moreover, the subsequent cyclization of benzylaminoacetals under acidic conditions leads virtually exclusively to the formation of the undesired isopavine or pavine structure [see, "Tetrahedron," S. F. Dyke et al, Vol 22, p. 3803 et seq. (1971)]. The cyclization of benzylaminoacetals can only be carried out preparatively after acylation of the nitrogen; 1,2-dihydroisoquinolines are formed here [see, Chem. Pharm. Bulletin, Vol 30, K. Yamada et al, p. 3197 et seq. (1982)].

In order to avoid the disadvantages in the preparation of 1-substituted isoquinoline derivatives according to Pomeranz-Fritsch, the corresponding 1-unsubstituted isoquinoline derivatives can first be prepared and from these, by reaction with benzoyl chloride in the presence of potassium cyanide, 1-cyano-2-benzoyl-1,2-dihydroisoquinolines can be prepared. By reaction with benzyl chlorides and hydrolysis under alkaline conditions, which is known in the literature as "Reissert synthesis," the corresponding 1-benzylisoquinoline derivatives can be obtained therefrom [see, G. Blaskó et al., Academic Press, Inc., The Alkaloids, Vol. 31, p. 1, et seq., (1987)].

The desired 1-alkylisoquinoline derivatives are, in general, produced by the processes mentioned in the form of racemates. Enantioselective syntheses, however, are also known. Thus, for example, an asymmetric total synthesis of (+)-reticuline was described, which starts from a 1-unsubstituted 1,2,3,4-tetrahydroisoquinoline derivative which is accessible by one of the reactions described above. The key step of this synthesis is the deprotonation of the 1,2,3,4-tetrahydroisoquinoline with tert-butyllithium at $-78°$ C. and the subsequent enantioselective alkylation of the 1-lithio-1,2,3,4-tetrahydroisoquinoline derivative at $-100°$ C., using an appropriately substituted benzyl bromide. Asymmetric induction is, in this case, executed by chiral formamidine. After this 5-step synthesis, (+)-reticuline was obtained, starting from the appropriately substituted phenylethylamine, in 98.6% ee (enantiomeric excess) and in a total yield of about 30% [see, Heterocycles, A. I. Meyers et al, Vol 28, p. 295, et seq. (1989)].

These known isoquinoline syntheses are, in general, multistep, and therefore uneconomical for carrying out on an industrial scale. In particular, the Pomeranz-Fritsch synthesis, by which 1-unsubstituted isoquinolines are relatively easily accessible, necessitates additional measures for the synthesis of 1-benzyl-1,2,3,4-tetrahydroisoquinolines and is, therefore, particularly complicated and time-consuming. Moreover, the insertion of enantioselective synthesis steps necessitates considerable outlay.

SUMMARY OF THE INVENTION

It is, therefore, an object of the present invention to provide a process for the preparation of 1-substituted isoquinoline derivatives which starts from easily accessible starting materials and which, in an economical manner, enables the preparation of the desired useful intermediates in a few steps.

The process, according to the invention, for the preparation of 1-alkyl-1,2,3,4-tetrahydroisoquinoline derivatives of the general formula (1)

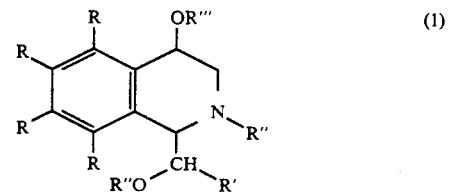

in which

R is H or halogen atoms, alkylamino, dialkylamino, acylamino, hydroxyl, alkoxy, aralkoxy or acyloxy radicals, or in each case, two of the R radicals together form an alkylenedioxy radical;

R' is an H atom or alkyl, acyl or aryl radical or aryl radical substituted by R radicals;

R" is H atoms, acyl, alkyl, aryl or silyl radicals, or two of the R" radicals together, form a diacyl radical;

R''' is H atoms or alkyl radicals comprising the steps of:

(a) reacting compounds of the formulae selected from the group consisting of:

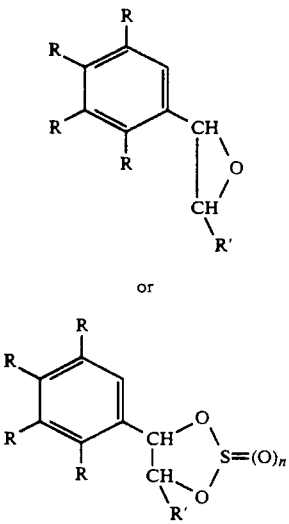

in which R and R' have the above-mentioned meaning, and n=1 or 2, with a compound (4) containing amino groups with ring opening, at temperatures in the range of from 50° C. to 200° C., in the presence of protic solvents or Lewis acids;

(b) protecting free OH groups and NH groups in the 2-phenyl-2-aminoethanol compounds (5) thus obtained alone or, in each case, together by protective groups selected from alkyl, acyl, silyl, and diacyl radicals; and (c) carrying out the ring closure with the formation of the 1-alkyl-1,2,3,4-tetrahydroisoquinoline derivatives (1) via an acetaldehyde or acetaldehyde diacetal group on the nitrogen, at temperatures in the range of from −30° C. to +40° C., in the presence of acids.

The compounds (2) employed as starting compounds in the first process step (a) in the process according to the invention, under which derivatives of styrene oxide are to be understood, can be prepared in a manner known per se by oxidation of appropriately substituted styrenes. Examples of oxidizing agents are sodium hypochlorite and m-chloroperoxybenzoic acid.

However, it is also possible to prepare optically active styrene oxide derivatives, for example, by enantioselective, catalytic epoxidation on chiral manganese salene complexes [see, Journal of American Chemical Society, Wei Zhang et al., Vol. 112, p. 2801, et seq. (1990)]. In this way, it is possible to use an optically active starting material such that in the subsequent carrying out of the process according to the invention, optically active compounds (1), which thus have enantiomer ratios not equal to 50:50, are obtained.

Under the starting compounds (3), analogues of the styrene oxide derivatives are to be understood, which instead of the oxide oxygen, have a cyclic sulfite or sulfate ester group. For their preparation, appropriately substituted styrenes can be dihydroxylated enantioselectively in a manner known per se using selected oxidizing agents (for example, N-methylmorpholine) on chiral osmium catalysts [see, Journal of American Chemical Society, E. N. Jacobsen et al., Vol. 110, p. 1968 et seq., 1988)].

The phenyl-1,2-ethanediols thus obtained can be esterified, for example, by action of thionyl chloride with the formation of the sulfite esters, and these can then be oxidized with the formation of the sulfate esters, for example, using sodium periodate as an oxidizing agent in the presence of ruthenium (III) chloride [see, Tetrahedron Letters, B. M. Kim et al., Vol 30, p. 655, et seq., (1989)].

In this case, too, the synthesis starts from optically active starting material, so that in the subsequent carrying out of the process according to the invention, optically active compounds (I) are obtained.

The ring opening of substituted starting compounds (2) or (3) (R' not equal to an H atom) takes place stereoselectively through the amine (4), i.e., depending on the configuration of the starting compound, the corresponding diastereomeric 2-phenyl-2-aminoethanol compounds (5) are obtained. For example, the erythro derivatives are obtained from compounds (2) or (3) having the trans-configuration, but the threo derivatives are obtained from compounds (2) or (3) having the cis-configuration. These diastereomers can be converted into one another if required by processes known per se, for example, by heating in a mixture of trifluoroacetic acid/trifluoroacetic anhydride [see, D. Seebach et al., Helv. Chim. Acta, Vol 70., p. 1357, et seq. (1987)].

The radicals R and R' in the starting compounds (2) and (3) have virtually the same meaning as in the desired isoquinoline derivatives (1).

Examples of R radicals of this type which, in each case, can be identical or different, are, apart from H atoms and hydroxyl groups, halogen atoms, such as fluorine, chlorine, bromine and iodine atoms; alkoxy radicals having 1-5 carbon atoms which can be straight-chain or branched, such as preferably methoxy and ethoxy radicals; aralkoxy radicals, such as the benzyloxy radical; alkylenedioxy radicals, such as methylenedioxy and ethylenedioxy radicals, and acyloxy radicals, such as acetoxy, trichloroacetoxy and benzoyloxy radicals.

Examples of R' radicals of this type are, apart from H atoms, alkyl radicals having 1-5 carbon atoms, which can be straight-chain or branched; acyl radicals, such as formyl, acetyl, propionyl, benzoyl, carboxymethyl, carboxyethyl and carboxybenzyl radicals; aryl radicals such a phenyl or phenyl radicals substituted by R radicals.

When carrying out the process according to the invention, the compounds (2) or (3) are reacted in process step (a), according to the definition, with the compound (4) containing amino groups, with opening of the epoxide ring of the compound (2) or of the cyclic sulfite or sulfate ester group of the compound (3).

Compounds (4) containing amino groups which can be used are ammonia and primary or secondary amines. The reaction is carried out, according to the definition, either in the presence of protic solvents or under anhydrous conditions in the presence of Lewis acids. The compounds (2) or (3) and (4) are, in this case, employed in a molar ratio of about 1:20 to 4:5, i.e., the reaction is carried out using an excess of amine.

Examples of protic solvents are alcohols, such as methanol, ethanol, iso-propanol, n-propanol, sec-butanol and tert-butanol, or the amine (4) employed. Ethanol and iso-propanol are preferably employed as protic solvents.

Inert solvents can additionally be co-used, to which are added about 5 to 50 vol-%, preferably about 10 vol-% of a protic solvent.

Examples of inert solvents are hydrocarbons, such as benzene and toluene; halogenated hydrocarbons, such as chlorobenzene, chloroform, dichloromethane and perchloroethylene or ethers, such as diethyl ether, tert-butyl methyl ether, tetrahydrofuran and dioxane, chloroform and dichloromethane being preferred.

The temperature of the reaction depends on the starting compounds used and the solvent selected. It is preferably carried out at temperatures in the range of from about 70° C. to 170° C.. The solvents can be distilled off from the reaction mixture in the course of the reaction, it being advantageous, in this case, if the inert solvent has a lower boiling point than the protic solvent.

When using low-boiling amines, such as ammonia or methylamine, the reaction is advantageously carried out in a pressure vessel.

The reaction can be catalyzed by additives, such as tetraalkylammonium halide, alumina or silica gel; this is generally known for epoxide openings. The reaction temperature is then lower.

Instead of the protic solvents, Lewis acids can be used which are advantageously employed in a stoichiometric ratio to the compounds (2) or (3). Examples of these are zinc (II) chloride, boron trifluoride, aluminum (III) isopropoxide and titanium (IV) isopropoxide. The reaction is advantageously carried out in one of the above-mentioned inert solvents under anhydrous conditions; the reaction temperature is, in this case, also lower, i.e., preferably at room temperature.

The use of the reaction components in the molar ratio amine:epoxide of 2:1, and the addition of about 10% by weight of silica gel (relative to epoxide employed) in the solvent mixture dichloromethane/isopropanol in the volume ratio 9:1 under a protective gas atmosphere, subsequent slow warming from 20° C. to 150° C., with simultaneous removal of the solvent mixture by distillation and cooling to 20° C. after reaction is complete, has proved particularly suitable for carrying out process step (a). The reaction mixture which remains is then extracted with solvent after working up by hydrolysis and evaporated.

If, in process step (a), the ring opening of the compounds (2) or (3) has been carried out using ammonia or a primary alkylamine, such as methylamine, 2-phenyl-2-aminoethanols or 2-phenyl-2-alkylaminoethanols, are obtained as compounds (5).

In order to introduce the acetaldehyde or acetaldehyde diacetal group on the N atom necessary for the isoquinoline ring closure in process step (c), these compounds must be reacted with, for example, haloacetaldehydes, such as chloro- or bromoacetaldehyde or haloacetaldehyde dialkyl acetal, such as chloro- or bromo-acetaldehyde dimethyl acetal, in a manner known per se in the presence of a base.

Examples of bases are inorganic bases, such as sodium hydride, sodium carbonate, sodium hydrogen carbonate or organic bases such as triethylamine, pyridine and dimethylaminopyridine.

The introduction of the acetaldehyde group can also be carried out by reaction with ethylene oxide and subsequent oxidation of the primary alcohol to the acetaldehyde derivative.

The reaction with ethylene oxide can be carried out in a pressure vessel, in the presence of a solvent, at temperatures of from about 70° C. to 130° C. Solvents and catalysts which can be used are the same as those mentioned in process step (a).

Oxidation to the acetaldehyde derivative is carried out in a manner known per se using dimethyl sulfoxide/oxalyl chloride.

The ring opening of the compounds (2) or (3) in process step (a) is preferably carried out, however, using primary or secondary amines which already contain the acetaldehyde group needed for the isoquinoline ring closure in process step (c). Among these compounds, aminoacetaldehyde dialkyl acetals, such as aminoacetaldehyde dimethyl acetal and alkylaminoacetaldehyde dialkyl acetals, such as methylaminoacetaldehyde dimethyl acetal are to be understood, in particular.

Before the isoquinoline ring closure reaction according to process step (c) can be undertaken, the free OH group in the 2-aminoethanol group of the compounds (5) must be protected in process step (b). If the compounds (5) are secondary amines in which a free H atom is present on the N atom, the NH group can also be protected.

The introduction of protective groups can be carried out in a manner known per se, for example, by alkylation with alkyl halides, such as methyl and ethyl iodide or benzyl chloride; by acylation with carbonyl halides, such a benzoyl chloride, pivaloyl chloride, pivaloyl-mandeloyl chloride or trichloroacetyl chloride; with carboxylic acid esters, such as chloroformic acid ester; with carboxylic anhydrides, such as acetic anhydride and trifluoroacetic anhydride. Reactions of this type are customarily carried out in the presence of a base, such as sodium carbonate, triethylamine and pyridine. Silylation, with the aid of alkoxy- or chlorosilanes is additionally known. When using substances yielding protective groups with two functional groups, OH and NH groups can also be jointly protected with ring formation, for example, by reaction with oxalyl chloride, with dialkyl carbonates, such as dimethyl carbonate, diethyl carbonate or ethylene carbonate or with N,N'-carbonyl-diimidazole.

After the free OH groups have been protected, in the manner described above, the isoquinoline ring closure reaction can be carried out according to the definition by process step (c) in the presence of acids.

Acids advantageously used are aqueous mineral acids, such as sulfuric acid, phosphoric acid and hydrochloric acid, concentrated hydrochloric acid having proved particularly suitable.

The acids are employed, together with water-miscible solvents, in the volume ratio from 10:90 to 90:10. Examples of water-miscible solvents are alkanols, such as methanol, ethanol, iso-propanol, n-propanol, sec-butanol and tert-butanol; ethers such as tetrahydrofuran and dioxane and also ketones, such as acetone and butan-2-one.

A mixture of acetone and concentrated hydrochloric acid in the volume ratio of from 40:60 to 80:20 has proved particularly suitable.

Instead of the aqueous mineral acids, however, Lewis acids can also be used together with anhydrous solvents. Examples of Lewis acids are titanium tetrachloride, boron trifluoride, boron trifluoride/diethyl ether complex compounds and tin tetrachloride, boron trifluoride/diethyl ether complex compounds and titanium tetrachloride having proved particularly suitable.

Examples of anhydrous solvents are hydrocarbons, such as hexane, petroleum ether and benzene; chlorohydrocarbons, such as dichloromethane, chloroform, dichloroethane and perchloroethylene; ethers such as diethyl ether, tert-butyl methyl ether, diethylene glycol dimethyl ether and tetrahydrofuran. Preferred anhydrous solvents are dichloromethane and diethyl ether.

The amount of the Lewis acid can be in the range from catalytic amounts up to stoichiometric amounts.

Both processes, i.e., both the carrying-out of the process with aqueous mineral acids and with Lewis acids under anhydrous conditions are characterized by the following reaction parameters: initial temperature of −20° C. to +10° C., preferably about −5° C.; and final temperature of +10° C. to 50° C., preferably room temperature; pressure: normal pressure, or autogenous pressure. If a temperature of +15° C. is attained in the reaction mixture, the reaction is monitored, for example, by thin layer chromatography and terminated when the acetal or the aldehyde has been consumed. The reaction time at room temperature can, in general, be about 0.5 to 15 hours, and the reaction is customarily complete after about 3 to 5 hours.

Process step (c) can be carried out batchwise or continuously, a continuous procedure being advantageous on the basis of the defined residence time and metering.

It has proved particularly suitable for process step (c), if the reaction components are combined at low temperature and then slowly warmed to room temperature, at which the actual cyclization takes place. The reaction mixture is finally worked up by alkaline hydrolysis and extracted, and the solvent is removed.

In process step (c), yields of more than 55% are, in general, achieved without detectable amounts of compounds having the undesired isopavine or pavine structure being formed.

The compounds of the general formula (1) thus prepared are 1,2,3,4-tetrahydroisoquinoline derivatives which contain an optionally substituted hydroxyalkyl radical in the 1-position of the isoquinoline ring and a hydroxyl or alkoxy group in the 4-position. Both hydroxyl groups can be present either in free form, or provided with protective groups.

The two hydroxyl groups or the hydroxyl groups provided with protective groups can be removed, either simultaneously or successively in subsequent reactions, from these compounds (1), which are useful intermediates.

This can be carried out, for example, by reduction with complex hydrides, the corresponding halogen-substituted isoquinolines being prepared by reaction with a halogenating agent, in the presence of a base, and these then being reduced with a hydride donor to the corresponding saturated compound.

Examples of halogenating agents are thionyl chloride, phosphorus trichloride, phosphorus pentachloride, phosphorus oxychloride, phosphorus tribromide, sulfonyl chloride and hydrogen bromide, thionyl chloride being preferred. Examples of bases are tertiary amines, such as triethylamine and pyridine. Examples of reducing agents are hydride donors, such as lithium aluminum hydride, sodium aluminum hydride, sodium bis(methoxy-ethoxy) aluminum hydride and sodium borohydride, lithium aluminum hydride and sodium borohydride being preferred. The reaction is expediently carried out under anhydrous conditions in the presence of inert solvents, tetrahydrofuran being preferred. 1-2 equivalents of halogenating agents, 1.1-2.2 equivalents of base and 1.2-10 equivalents of reducing agent are employed per OH group to be reduced.

In general terms, the hydroxyl compound (1) is treated with the halogenating agent in the inert solvent at preferably 0° C. and the halogen compound formed in situ is then immediately reduced to the saturated compound at 0° C. to 20° C. After working-up by hydrolysis, the mixture is extracted with a solvent and evaporated.

The corresponding tosylates can also be prepared from the benzyl alcohol derivatives in an analogous manner, and these can then be reduced.

The corresponding acetates can also be prepared from the benzyl alcohol derivatives, in an analogous manner, and these can then be reduced in a manner known per se, for example, with sodium borohydride in the presence of nickel acetate [see, *Synthetic Communications*, Yun He et al., Vol. 19, p. 3051, et seq., (1989)].

Instead of the reduction With complex hydrides, however, a catalytic hydrogenation can also be carried out. For the reduction of 4-hydroxy or 4-alkoxy substituents, the hydrogenation must be carried out in the presence of an acid. Examples of $H_2$ sources are molecular hydrogen, which is preferred, but also hydrogen donors (transfer hydrogenation), such as ammonium formate, formic acid/triethylamine and alcohols. Examples of catalysts are noble metals, such as palladium and platinum or Raney nickel as a metallic precipitate and salts or complex salts, such as $PdCl_2$, $PdO$, $PtO_2$ on customary supports, such as active carbon; a palladium catalyst containing about 10% Pd on active carbon having proved particularly suitable. Examples of acids are mineral acids, such as hydrochloric acid, sulfuric acid or phosphoric acid or carboxylic acids, such as formic acid, acetic acid, propionic acid, oxalic acid, malonic acid, citric acid, malic acid and salicylic acid, acetic acid and oxalic acid being preferred. Preferred solvents are protic solvents, or those which are miscible with water. Examples of such solvents are tetrahydrofuran, methanol, ethanol and isopropanol. They can be used as such or mixed with water. The molecular hydrogen can be used at a pressure in the range of from about 0.1-15.0 MPa; the temperature is advantageously in the range of from 50° C. to 100° C.

If a tertiary nitrogen atom is present in the intermediates, according to the general formula (1), i.e., for example, the nitrogen is substituted by methyl-1,2,3,4,-tetrahydroisoquinolines of the reticuline type are obtained, as a result of these reductive measures, which, for their part, can be used as building blocks, for example, for morphine syntheses. Examples of compounds of this type are reticuline, laudanosine, laudanosoline, carnegine and 6-(dimethylamino)-1-(3-hydroxy-4-methoxybenzyl)-1,2,3,4-tetrahydroisoquinoline. In the presence of a secondary nitrogen atom, i.e., a free NH group, 1,2,3,4-tetrahydroisoquinolines of the norreticuline type are obtained. Examples of compounds of this type are norreticuline, norlaudanosine, salsolidine, salsoline and salsolinol.

By means of acid-catalyzed hydrolysis, both the acyl and other protective groups can additionally be removed from compounds (1) which carry an acyl protective group on the nitrogen and the hydroxyl groups can be removed simultaneously, so that isoquinolines of the papaverine type are obtained directly in this manner. The reaction is advantageously carried out in an inert solvent, such as toluene or xylene, and p-toluenesulfonic acid is preferably used as the acid. The reaction is carried out at elevated temperature, preferably at the reflux temperature of the solvent.

Final products obtained, in this case, are aromatized isoquinolines, for example, of the papaverine type.

It is additionally possible, under certain conditions that 1,2-dihydroisoquinoline derivatives are obtained directly on altering the process according to the invention by combining steps (b) and (c) with simultaneous removal of the hydroxyl group in the 4-position. Thus, for example, 1,2-dihydroisoquinoline derivatives in which the OH group in the 4-position has already been removed during the ring closure are obtained directly, in one process step, by means of a combined acylation and cyclization of compounds (5), which are secondary amines, i.e., in which a free H atom is present on the nitrogen atom after the ring opening according to process step (a), such as aminoacetaldehyde dialkyl acetals, in the presence of acylating agents, such as carbonyl halides, in particular, benzoyl chloride, and in the presence of bases, such as tertiary amines and pyridine under anhydrous conditions. Aromatic isoquinolines, such as papaverine, can be obtained directly from these by subsequent further reduction to remove the N- and O-acyl group with, for example, hydrazine hydrate, assuming the substituents are appropriate. Aromatic isoquinoline derivatives, for example, of the papaverine type, can also be obtained directly, however, from correspondingly substituted 1,2-dihydroisoquinoline derivatives by reaction with compounds having an acidic action, such as mineral acids, preferably hydrochloric acid, in the presence of water-miscible solvents, preferably at reflux temperature.

BRIEF DESCRIPTION OF THE DRAWINGS

Other objects and features of the present invention will become apparent from the following detailed description considered in connection with the accompanying drawing which discloses one embodiment of the present invention. It should be understood, however, that this drawing is designed for the purpose of illustration only and not as a definition of the limits of the invention.

The process steps in the process according to the invention for the preparation of the compounds (1) and possible subsequent reactions are represented schematically, in simplified form, in the figure of the drawings.

DETAILED DESCRIPTION OF THE PREFERRED EMBODIMENT

EXAMPLES

Preparation of the Starting Compounds:

EXAMPLE 1 rel-(S,S)-3,3'-Dibenzyloxy-4,4'-dimethoxy-stilbene oxide

Mixture: 66.7 g 150 mmol) of 3,3'-dibenzyloxy-4,4'-dimethoxystilbene, 1500 ml of dichloromethane, 1500 ml of sodium hydrogen carbonate solution, 667 mg (1.5 mmol) of nickel-salene, 1.334 g (4.3 mmol) of benzyltributylammonium chloride, 250 ml of sodium hypochlorite solution (13% active chlorine).

Procedure: The sodium hypochlorite solution was added dropwise to the mixture of the other reagents at 5° C. to 10° C. in the course of 2 h, and the mixture was subsequently stirred for 2 h. For working-up, the organic phase was separated off and filtered through a short silica bed. The epoxide solution thus prepared is directly available for further reactions or can be concentrated in a rotary evaporator and recrystallized from ethanol.

Yield: 66.5 g (96.4).

Anal. data: $R_f$ (dichloromethane/methanol 100:0)=0.50; $R_f$ (starting material)=0.90; m.p.: 102° (ethanol).

EXAMPLE 2 rel-(S,S)-3,3',4,4'-Tetramethoxystilbene oxide

Mixture: 50.0 g 166 mmol) of 3,3',4,4'-tetramethoxystilbene, 1000 ml of dichloromethane, 1000 ml of sodium hydrogen carbonate solution, 64.0 g (185 mmol) of m-chloroperoxybenzoic acid (about 50% strength).

Procedure: The m-chloroperoxybenzoic acid, dissolved in 200 ml of dichloromethane, was slowly added dropwise to the tetramethoxystilbene in dichloromethane and sodium hydrogen carbonate (about 4 h). The organic phase was separated off after 1 h. The epoxide solution thus prepared is available for further reactions.

Yield: the reaction proceeded quantitatively.

Anal. data: $R_f$(dichloromethane)=0.33. $R_f$(starting material)=0.53.

EXAMPLE 3

3,4-Dimethoxystyrene oxide

Mixture: 27.2 g (160 mmol) of 3,4-dimethoxystyrene, 600 ml of dichloromethane, 220 ml of sodium hydrogen carbonate solution, 7.1 g of benzyltributylammonium chloride, 1.15 g (3.5 mmol) of nickel-salene, 900 ml of 13% strength sodium hypochlorite solution.

Procedure: Dimethoxystyrene, benzyltributylammonium chloride and nickel-salene catalyst were initially introduced into dichloromethane and sodium hydrogen carbonate, and the sodium hypochlorite solution was added dropwise in the course of 4 h. The mixture was then stirred for 1 h, and the organic phase was separated off, washed with saturated sodium chloride solution and filtered through silica gel. The epoxide solution thus prepared was used directly for further reactions.

Yield: the reaction proceeded quantitatively.

Anal. data: $R_f$(dichloromethane)=0.33; $R_f$(starting material)=0.62.

EXAMPLE 4

(1S,2S)-1,2-bis(3'-Benzyloxy-4'-methoxy-phenyl)ethanediol

Mixture: 50 g 10 mmol) of 3,3'-dibenzyloxy-4,4'-dimethoxystilbene, 0.49 g (1.66 mmol) of osmium trichloride, 2.57 g (5.33 mmol) of 4-chlorobenzoyldihydroquinidine, 22.4 (191 mmol) of N-methylmorpholine-N-oxide, 3 l of acetone/water (9:1), 30 g of silica gel.

Procedure: The stilbene, mixed with the silica gel, was continuously metered as continuously as possible into the mixture of the other reagents, at room temperature in the course of 48 h. For working-up, the silica gel was filtered off. The solution was concentrated and the residue was heated under reflux with 400 ml of tetrahydrofuran/saturated, sodium bisulfite solution (1:1) for 2h. The organic phase was separated off, and the aqueous phase was brought to pH=9 with saturated sodium hydrogen carbonate solution and extracted with ethyl acetate. The combined organic phases were concentrated and chromatographed (dichloromethane/methanol 95:5).

Yield: 47.3 g (88.4%).

Anal. data: $R_f$ (dichloromethane/methanol 95:5)=0.38; $R_f$(starting material)=0.95. $[\alpha]_D = +120.3°$ (c=1, dichloromethane, 92.7% ee).

EXAMPLE 5

(4S,5S)-4,5-bis(3'-Benzyloxy-4'-methoxy-phenyl)-2-oxo-1,3,2-dioxathiolane

Mixture: 30.74 g 63.2 mmol) of (1S,2S)-1,2-bis(3'-benzyloxy-4'-methoxyphenyl)ethanediol ($[\alpha]_D = +120.3°$ (c=1, $CH_2Cl_2$) 92.7% ee), 150 ml of dichloromethane, abs., 33.5 ml (240 mmol) of triethylamine, 6.9 ml (94.6 mmol) of thionyl chloride in 10 ml of dichloromethane abs.

Procedure: Diol, dissolved in dichloromethane and triethylamine, was initially introduced at 0° C. under $N_2$, and thionyl chloride, diluted with dichloromethane, was slowly added dropwise (exothermic reaction). Working-up (also at 0° C.) was carried out after 40 min at 0° C. by addition of 150 ml of diethyl ether and subsequent extraction by shaking, twice with 75 ml of water and once with 75 ml of saturated NaCl solution. The organic phase was dried over magnesium sulfate, concentrated in a rotary evaporator, again thoroughly concentrated with dichloromethane and dried in a high vacuum for 1 h.

Yield: quantitative.

Anal. data: $R_f$ (dichloromethane/methanol 98:2)=0.76; $R_f$ (starting material)=0.24. $[\alpha]_D=171.4°$ (c=1, dichloromethane)

EXAMPLE 6

(4S,5S)-4,5-bis(3'-Benzyloxy-4'-methoxyphenyl)-2,2-dioxo-1,3,2-dioxathiolane

Mixture: 33 g (63 mmol) of (4S,5S)-4,5-bis(3'-benzyloxy-4'-methoxyphenyl)-2-oxo-1,3,2-dioxathiolane, 300 ml of dichloromethane/acetonitrile 1:1, 200 ml of ice-water, 72.7 mg (0.35 mmol) of ruthenium (III) chloride hydrate, 26.83 g (125.4 mmol) of sodium metaperiodate.

Procedure: Ice-water, ruthenium (III) chloride and $NaIO_4$ were rapidly added successively to a solution of the cyclic sulfite in dichloromethane/acetonitrile 1:1 at 0° C. and under a protective gas atmosphere, and the mixture was subsequently stirred, at this temperature, for 1 h. Working-up was carried out by adding 150 ml of diethyl ether, extracting by shaking twice with 75 ml portions of water, in each case, and extracting by shaking once with 75 ml of saturated sodium chloride solution. The organic phase was dried over magnesium sulfate.

Anal data: $[\alpha]_D = 183.6°$ (c=1, dichloromethane). Process Step (a):

EXAMPLE 7 rel-(1S,2R)-1,2-bis(3'-Benzyloxy-4'-methoxyphenyl)-2-[(2",2"-dimethoxyethyl)-methyl-amino]ethanol Mixture: 51.7 g (0.11 mol) of rel-(S,S)-3,3'-dibenzyloxy-4,4'-dimethoxystilbene oxide, 1800 ml of dichloromethane, 100 ml of 2-butanol, 25 ml (0.19 mol) of methylaminoacetaldehyde dimethyl acetal, 5 g of silica gel Procedure: The stilbene oxide, dissolved in dichloromethane and 2-butanol, was slowly heated to 120° C. together with methylaminoacetaldehyde dimethyl acetal and silica gel (about 8 h), first dichloromethane, then butanol distilling off. Working-up was carried out by filtration and extraction by shaking twice with water/dichloromethane. The organic phase was concentrated twice with toluene in a rotary evaporator and purified by chromatography (dichloromethane/methanol 98:2).

Yield: 50.9 g (79%).

Anal. data: $R_f$ (dichloromethane/methanol 97:3)=0.36. $R_f$ (starting material, dichloromethane)=0.37.

EXAMPLE 8 rel-(1S,2R)-1,2-bis(3'-Benzyloxy-4'-methoxyphenyl)-2-[(2",2"-dimethoxyethyl)methyl=amino]ethanol Mixture: 4.68 g (10 mmol) of rel(S,S)-3,3'-dibenzyloxy-4,4'-dimethoxystilbene oxide, 3.57 g (3.83 ml, 30 mmol) of methylaminoacetaldehyde dimethyl acetal, 3.41 g (3.57 ml, 12 mmol) of titanium (IV) tetraisopropoxide, 200 ml of dichloromethane, anhydrous.

Procedure: Titanium (IV) tetraisopropoxide, dissolved in a little dichloromethane, was slowly added dropwise at −20° C. to epoxide and methylaminoacetaldehyde dimethyl acetal, dissolved in anhydrous dichloromethane. The mixture was warmed to room temperature after 30 min and subsequently stirred for a further 2 h. Working-up was carried out by washing the organic phase with saturated sodium hydrogen carbonate solution. The mixture was concentrated in a rotary evaporator after washing five times with water and finally with saturated sodium chloride solution. The desired product was obtained in the form of an oil.

Yield: 4.79 g (83%).

Anal. data: $R_f$ (dichloromethane/methanol 97:3)=0.36; $R_f$(starting material)=0.85.

EXAMPLE 9

(1S,2R)-1,2-bis(3'-Benzyloxy-4'-methoxyphenyl)-2-[(2",2"-dimethoxyethyl)-methyl-amino]ethanol Mixture: about 33 g (63 mmol) of (4S,5S)-4,5-bis(3'-benzyloxy-4'-methoxyphenyl)-2,2-dioxo-1,3,2-dioxathiolane, 300 ml of dichloromethane, 50 ml of 2-butanol, 48.4 ml (377 mmol) of methylaminoacetaldehyde dimethyl acetal.

Procedure: The cyclic sulfate, dissolved in dichloromethane and 2-butanol, was slowly heated to 150° C. (about 8 h), together with methylaminoacetaldehyde dimethyl acetal, first dichloromethane, then butanol distilling off. The reaction mixture was kept at this temperature for 1 h, treated with 20 percent strength aqueous sulfuric acid and stirred at 0° C. for a further 30 minutes. The mixture was then brought to pH=10, with 20 percent sodium hydroxide solution and extracted with dichloromethane. Further purification can be carried out by chromatography(dichloromethane/methanol 97:3).

Yield: 18.2 g (57%).

Anal. Data: $R_f$ (dichloromethane/methanol 97:3)=0.39. $[\alpha]_D = -111°$ (c=1, dichloromethane).

EXAMPLE 10

(1S,2R)-1,2-bis(3'-Benzyloxy-4'-methoxyphenyl)-2-[(2",2"-dimethoxyethyl)amino]-ethanol Mixture: 187.2 g (0.4 mol) of rel-(S,S)-3,3'-dibenzyloxy-4,4'-dimethoxystilbene oxide, 210 g (2 mol) of aminoacetaldehyde dimethyl acetal, 5 l of dichloromethane, 3 l of ethanol.

Procedure: The stilbene oxide, dissolved in dichloromethane and ethanol, was slowly heated to 150° C. (about 8 h) together with methylaminoacetaldehyde dimethyl acetal, first dichloromethane and then ethanol being distilled off to a residual volume of 1.3 l. Working-up was carried out by extracting three times by shaking with water/dichloromethane. After removing the solvent, the product crystallized out and was filtered off with suction.

Yield: 132 g 57.6%).

Anal. Data: R$_f$ (dichloromethane/methanol 97:3)=0.26; R$_f$(starting material)=0.86. m.p 117° C.

EXAMPLE 11(A)

rel-(1S,2R)-1,2-bis(3'-Benzyloxy-4'-methoxyphenyl)-2-aminoethanol

Mixture: 1.0 g (2.1 mmol) of rel-(S,S)-3,3'-dibenzyloxy-4,4'-dimethoxystilbene oxide, 15 ml of EtOH, abs., 15 ml of ammonia.

Procedure: Ammonia was condensed into a receiver for the epoxide in ethanol. After 7 h at 80° C. in an autoclave, the reaction mixture was concentrated in a rotary evaporator and chromatographed (dichloromethane/methanol 9:1).

Yield: 0.68 g (67%).

Anal. Data: R$_f$ (dichloromethane/methanol 9:1)=0.36; R$_f$(starting material)=0.90.

EXAMPLE 11(B)

rel-(4R,5s)-4,5-bis(3'-Benzyloxy-4'-methoxyphenyl)oxazolidine-2-one

Mixture: 1.0 g (2.06 mmol) of rel-(1S,2R)-1,2-bis(3'-benzyloxy-4'-methoxyphenyl)-2-aminoethanol, 334 mg (2.05 mmol) of carbonyldiimidazole, 20 ml of toluene.

Procedure: The reaction mixture was heated under reflux for 2 h. Working-up was carried out by concentrating in a rotary evaporator, and purification by chromatography (dichloromethane/methanol 95:5).

Yield: 905 mg (86%).

Anal Data: R$_f$ (dichloromethane/methanol 9:1)=0.53; R$_f$(starting material)=0.08.

EXAMPLE 11(C)

rel-(4R,5S)-4,5-bis(3'-Benzyloxy-4'-methoxyphenyl)-3-(2'-hydroxyethyl)oxazolidine-2-one Mixture: 100 mg of rel-(4R,5S)-4,5-bis(3'-benzyloxy-4'-methoxyphenyl)oxazolidin-2-one, 5 ml of ethylene oxide, 15 ml of tetrahydrofuran, 5 mg of methylammonium chloride.

Procedure: The reaction mixture was stirred in a pressure vessel at a temperature of 120° C. for 10 h. It was then concentrated in a rotary evaporator and chromatographed (dichloromethane/methanol 95:5).

Yield: 80 mg (73%).

Anal. Data: R$_f$ (dichloromethane/methanol 95:5)=0.62; R$_f$(starting material)=0.75.

EXAMPLE 12(A)

rel-(18,2R)-1,2-bis(3'-Benzyloxy-4'-methoxyphenyl)-2-methylaminoethanol

Mixture: 39 g (80 mmol) of rel-(S,S)-3,3'-dibenzyloxy-4,4'-dimethoxystilbene oxide, 250 ml of methylamine (30 percent in methanol), 100 ml of dichloromethane.

Procedure: The reaction mixture was rocked in a rocking autoclave of 500 ml capacity for 20 h at a jacket temperature of 100° C. Working-up was carried out by concentrating the reaction solution in a rotary evaporator and extracting by shaking three times with water/dichloromethane. The crude product was then chromatographed (dichloromethane/methanol 95:5).

Yield: 32.0 g (64%).

Anal Data: R$_f$ (dichloromethane/methanol 95:5)=0.25; R$_f$(starting material)=0.09.

EXAMPLE 12(B)

rel-(1S,2R)-1,2-bis(3'-Benzyloxy-4'-methoxyphenyl)-2-[(2'',2''-dimethoxyethyl)-methylamino]ethanol Mixture: 1.40 g 2.8 mmol) of rel-(1S,2R)-1,2-bis(3'-benzyloxy-4'-methoxyphenyl)-2-methylaminoethanol, 0.43 ml (0.61 g, 3.6 mmol) of bromoacetaldehyde dimethyl acetal, 0.71 g (8.4 mmol) of sodium hydrogen carbonate.

Procedure: The methylaminoethanol was heated to 130° C. for 4 h together with the bromoacetaldehyde dimethyl acetal and sodium hydrogen carbonate. The residue was taken up in dichloromethane, and the solution was washed first with sodium hydrogen carbonate and then with sodium chloride solution and concentrated in a rotary evaporator. The residue can be chromatographed for purification.

Yield: 1.43 g (87%).

Anal. Data: R$_f$ (dichloromethane/methanol 9:1)=0.85; R$_f$(starting material)=0.28.

EXAMPLE 13 rel-(1S,2R)-1,2-bis(3',4'-dimethoxyphenyl)-2-[(2'',2''-dimethoxyethyl)amino]ethanol Mixture: 57 g (0.17 mol) of 3,3',4,4'-tetramethoxy-stilbene oxide, 120 ml (1.1 mol) of aminoacetaldehyde dimethyl acetal, 1.5 l of dichloromethane, 80 ml of 2-butanol.

Procedure: The reaction mixture was slowly heated to a temperature of 130° C. under a protective gas atmosphere, the solvents distilling off. It was then stirred at this temperature for one hour. Working-up was carried out by extracting several times by shaking with dichloromethane/water. The organic phase was concentrated in a rotary evaporator and purified by column chromatography (dichloromethane/methanol 98:2).

Yield: 63.0 g (88%).

Anal. Data: R$_f$ (dichloromethane/methanol 95:5)=0.32; R$_f$(starting material)=0.90.

EXAMPLE 14

2-(3',4'-Dimethoxyphenyl)-2-[(2'',2''-dimethoxyethyl)amino]ethanol, 1-(3',4'-Dimethoxyphenyl)-2-[(2'',2''-dimethoxyethyl)amino]ethanol Mixture: 28.6 g (0.16 mol) of 3,4-dimethoxystyrene oxide, 50 ml of aminoacetaldehyde dimethyl acetal, 5 g of silica gel, 500 ml of dichloromethane, 100 ml of ethanol.

Procedure: The reaction mixture was slowly heated to a temperature of 130° C. under a protective gas atmosphere, the solvents distilling off. It was then stirred at this temperature for one hour. Working-up was carried out by extracting several times by shaking with dichloromethane/water. The organic phase was concentrated in a rotary evaporator. The diastereomers (1:1) were separated by chromatography (dichloromethane/-methanol 95:5).

Total Yield: 29.6 g (65%).

Anal. Data: R$_f$ (dichloromethane/methanol 95:5)=0.10; and 0.18; R$_f$(starting material)=0.90.

Process Step (b):

EXAMPLE 15 rel-(1'S,2'R)
1',2'-bis(3''-Benzyloxy-4''-methoxyphenyl)-2'-((2'''-dimethoxyethyl)-methylamino)ethyl benzoate Mixture: 86.6 g (0.15 mol) of (1S,2R)-1,2-bis(3'-benzyloxy-4'-methoxyphenyl)-2-[(2'',2''-dimethoxyethyl)-methylamino]ethanol, 600 ml of dichloromethane, abs., 103 ml (1.27 mol) of pyridine, 103 ml (0.67 mol) of benzoyl chloride.

Procedure: The reaction mixture was stirred at RT for 18 h, with exclusion of air. Working-up was carried out by concentrating in a high vacuum at 60° C. in a rotary evaporator and twice rinsing thoroughly with toluene and dichloromethane. The crude product was taken up in dichloromethane and cautiously stirred thoroughly with saturated aqueous sodium hydrogen carbonate solution. The organic phase was extracted by shaking twice more with sodium hydrogen carbonate solution, concentrated in a rotary evaporator and chromatographed (dichloromethane/methanol 99:1).

Yield: 59 g (62%).

Anal. Data: $R_f$ (dichloromethane/methanol 98:2)=0.4; $R_f$(starting material)=0.16.

EXAMPLE 16(A)

rel-(1'S,2'R)
1',2'-bis(3''-Benzyloxy-4''-methoxyphenyl)-2'-((2'''-dimethoxyethyl)-methylamino)ethyl acetate Mixture: 25.4 g (44.3 mmol) of (1S,2R)-1,2-bis(3'-benzyloxy-4'-methoxyphenyl)-2-[(2'',2''-dimethoxyethyl)-methylamino]ethanol, 500 ml of dichloromethane, abs., 20 ml (248 mmol) of pyridine, 24 ml (254 mmol) of acetic anhydride.

Procedure: The reaction mixture was stirred at RT for 18 h, with exclusion of air. Working-up was carried out by concentrating the crude product in a high vacuum at 60° C. in a rotary evaporator, taking up twice in toluene and dichloromethane, in each case, and concentrating the organic phase in a rotary evaporator. The residue can be chromatographed for purification (dichloromethane/methanol 98:2).

Yield: 21.8 g (80%).

Anal. Data: $R_f$ (dichloromethane/methanol 97:3)=0.53; $R_f$(starting material)=0.34.

EXAMPLE 16(B)

(1'S,2'R) bis
(3''-Benzyloxy-4''-methoxy-phenyl)-2'-((2'''-dimethoxyethyl)methylamino)-ethyl acetate The reaction was carried out as described for the racemic compound. $[\alpha]_D = -41.3°$ (c=1, dichloromethane, ee=92.7%).

EXAMPLE 17 rel-(4R,5s)-4,5-bis(3'-Benzyloxy-4'-methoxyphenyl)-3-(2',2'-dimethoxyethyl)oxazolidin-2-one Mixture: 500 mg (0.87 mmol) of rel-(1S,2R)-1,2-bis(3'-benzyloxy-4'-methoxyphenyl)-2-[(2',2'-dimethoxyethyl)amino]ethanol, 320 mg (2.0 mmol) of carbonyldiimidazole, 20 ml of toluene.

Procedure: The reaction mixture was heated under reflux for one hour and concentrated in a rotary evaporator. The crude product was taken up in dichloromethane, and extracted by shaking twice with water and once with sodium chloride solution. The organic phase was concentrated in a rotary evaporator and chromatographed (dichloromethane/methanol 97:3).

Yield: 337 mg (63%).

Anal. Data: $R_f$ (dichloromethane/methoanol 97:3)=0.6; $R_f$(starting material)=0.1.

EXAMPLE 18 rel-(1'S,2'R)
1',2'bis(3''-Benzyloxy-4''-methoxyphenyl)-2'-(acetyl-(2''',2'''-dimethoxy-ethyl)amino)ethyl acetate Mixture: 6.35 g (10 mmol) of rel-(1S,2R)-1,2-bis(3'-Benzyloxy-4'-methoxyphenyl)-2-[(2',2'-dimethoxyethyl)amino]ethanol, 100 ml of dichloromethane abs., 8 ml (99.2 mmol) of pyridine, 8.8 ml (93.2 mmol) of acetic anhydride.

Procedure: The reaction mixture was stirred at RT for 18 h with exclusion of air. Working-up was carried out by concentrating in a high vacuum at 60° C. in a rotary evaporator, concentrating twice with toluene in a rotary evaporator and isolation of the product by column chromatography (dichloromethane/methanol 99:1).

Yield: 6.91 g (95%).

Anal. Data: $R_f$ (dichloromethane/methanol 97:3)=0.58; $R_f$(starting material)=0.46.

EXAMPLE 19 rel-(1'S,2'R)
1',2'-bis(3''-Benzyloxy-4''-methoxyphenyl)-2'-((2''',2'''-dimethoxyethyl)-pivaloylamino)ethyl pivalate Mixture: 5.0 g (8.73 mmol) of rel-(1S,2R)-1,2-bis(3'-benzyloxy-4'-methoxyphenyl)-2-[(2',2'-dimethoxyethyl)amino]ethanol, 15 ml (187 mmol) of pyridine, 15 ml (122 mmol) of pivaloyl chloride.

Procedure: The acid chloride was added dropwise to the amino ethanol, dissolved in pyridine, and the mixture was stirred at RT for 18 h. Working-up was carried out by concentrating at 60° C. and at 0.01 mm Hg in a rotary evaporator, and concentrating twice with toluene and dichloromethane in a rotary evaporator. Final purification was carried out by chromatography (dichloromethane/methanol 98:2).

Yield: 5.70 g (88%).

Anal. Data: $R_f$ (dichloromethane/methanol 97:3)=0.32; $R_f$(starting material)=0.08.

EXAMPLE 20

(2R,1'S,2'R)
1',2'-bis(3''-Benzyloxy-4''-methoxyphenyl)-2'-((2''',2'''-dimethoxyethyl)-methylamino)ethyl
O-pivaloylmandelate (2R,1'R,2'S)
1',2'-bis(3''-Benzyloxy-4''-methoxyphenyl)-2'-((2''',2'''-dimethoxyethyl)methylamino)ethyl
O-pivaloylmandelate Mixture: 7.0 g (11.9 mmol) of rel-(1S,2R)-1,2-bis(3'-benzyloxy-4'-methoxyphenyl)-2-((2',2'-dimethoxyethyl)methylamino)ethanol, 3.0 g (11.8 mmol) of R-pivaloylmandeloyl chloride, 100 ml of pyridine.

Procedure: Pivaloylmandeloyl chloride was added dropwise at 0° C. to the solution of the aminoethanol in pyridine. The mixture was then stirred at room temperature for 1 h, concentrated in a rotary evaporator and chromatographed (dichloromethane/methanol 99:1).

Yield: 9 g (94%).

Anal. Data: $R_f$ (dichloromethane/methanol 97:3); (2R,1'S,2'R)-isomer: $R_f=0.75$; $[\alpha]_D=-9°$ (c=1, dichloromethane), (2R,1'R,2'S)-isomer: $R_f=0.66$; $[\alpha]_D=+2.7°$ (c=1, $CH_2Cl_2$), starting material: $R_f=0.42$.

EXAMPLE 21

2'-(3'',4''-Dimethoxyphenyl)-2'-(acetyl-(2'''-dimethoxyethyl)amino)ethyl acetate Mixture: 5.0 g (17.5 mmol) of 2-(3',4'-dimethoxyphenyl)-2-[(2'',2''-dimethoxyethyl)amino]-ethanol, 20 ml of pyridine, 20 ml of acetic anhydride.

Procedure: The reaction mixture was stirred at room temperature for 3 h, with exclusion of air. Working-up was carried out by concentrating twice at 60° C. in a high vacuum with toluene in a rotary evaporator and isolation of the product by column chromatography (dichloromethane/methanol 95:5).

Yield: 5.45 g (85%).

Anal. Data: $R_f$ (dichloromethane/methanol 9:1)=0.40; $R_f$(starting material)=0.30.

EXAMPLE 22 rel-(5R,6s)-5,6-bis(3'-Benzyloxy-4'-methoxyphenyl)-4-(2',2'-dimethoxyethyl)-1,4-oxazine-2,3-dione Mixture: 200 mg (0.35 mmol) of rel-(1S,2R)-1,2-bis(3'-benzyloxy-4'-methoxyphenyl)-2-((2',2'-dimethoxyethyl)amino)ethanol, 50 mg 0.39 mmol) of oxalyl chloride, 30 mg (0.39 mmol) of pyridine, 20 ml of dichloromethane, abs.

Procedure: Oxalyl chloride in dichloromethane was added dropwise to the aminoethanol dissolved in pyridine and dichloromethane. The mixture was concentrated in a rotary evaporator after 1 h and extracted by shaking with dichloromethane/saturated sodium hydrogen carbonate solution. The organic phase was concentrated in a rotary evaporator and chromatographed (dichloromethane/methanol 98:2)

Yield: 200 mg (91%).

Anal. Data: $R_f$ (dichloromethane/methanol 97:3)=0.69; $R_f$(starting material)=0.36.

EXAMPLE 23 rel-(1R,2R) 1',2'-bis(3'',4'''-Dimethoxyphenyl)-2-methylaminoethyl pivalate

Mixture: 2.15 g (5 mmol) of rel-(1R,2S) N-[1,2-bis-(3',4'-dimethoxyphenyl)-2-ethanol]pivalamide, 2 ml (2.97 g, 14.1 mmol) of trifluoroacetic anhydride, 18 ml of trifluoroacetic acid Procedure: The pivaloyl amide was heated under reflux for 2 h in a mixture of trifluoroacetic acid/trifluoroacetic anhydride. After cooling to room temperature, ice was added, and the mixture was rendered alkaline with potassium carbonate and extracted with dichloromethane. The product was purified by chromatography.

Yield: 1.78 g (83%).

Anal. Data: $R_f$ (dichloromethane/methanol 97:3)=0.40; $R_f$(starting material)=0.28.

Process Step (c):

EXAMPLE 24(A)

rel-(αs,1'R) α-(7'-Benzyloxy-4-hydroxy-6'-methoxy-1',2',3',4'-tetrahydroisoquinolin-1'-yl)-3-benzyloxy-4-methoxybenzyl acetate Mixture: 27.4 g (44.3 mmol) of rel-(1'S,2'R) bis(3''-benzyloxy-4''-methoxyphenyl)-2'-((2'''-dimethoxyethyl)methylamino)ethyl acetate, 102 ml of acetone, 68 ml of concentrated hydrochloric acid.

Procedure: The concentrated hydrochloric acid was slowly added dropwise ($T^{max}$ 10° C.) at −20° C. under a protective gas atmosphere to the aminoethanol, dissolved in acetone. The cooling was then removed, and the mixture was stirred at RT for about a further 8 h; TLC checking. The reaction was monitored by thin-layer chromatography and immediately terminated when the starting material had reacted completely. Working-up was carried out by addition of dichloromethane and neutralization with concentrated ammonia solution. Saturated sodium hydrogen carbonate solution was then added, and the organic phase is separated off and extracted twice more by shaking with the same sodium hydrogen carbonate solution and concentrated in a rotary evaporator. The crude product was purified through a filtration column (dichloromethane/methanol 98:2).

Yield: 22.1 g (87%).

Anal. Data: $R_f$(dichloromethane/methanol 97:3) 0.25 4'S-isomer; 0.42 4'R-isomer; 0.50 starting material.

EXAMPLE 24(B)

(αS,1'R,4'S) α-(7'Benzyloxy-4'-hydroxy-6'-methoxy-1',2',3',4'-tetrahydroisoquinolin-1'-yl)-3-benzyloxy-4-methoxybenzyl acetate The compound was prepared as described for the racemate. $[\alpha]_D=-2.3°$ (c=1, dichloromethane); ee=92.7°.

EXAMPLE 25 rel-(αS,1'R) α-(7'Benzyloxy-4'-hydroxy-6'-methoxy-1',2',3',4'-tetrahydroisoquinolin-1'-yl)-3-benzyloxy-4-methoxybenzyl acetate rel-(αS,1'R) α-(7'-Benzyloxy-4',6'-dimethoxy-1',2',3',4'-tetrahydroisoquinolin-1'-yl)-3-benzyloxy-4-methoxybenzyl acetate Mixture: 3.14 g (5 mmol) of rel-(1'S,2'R) bis(3''-benzyloxy-4''-methoxyphenyl)-2'-((2'''-dimethoxyethyl)-methylamino)ethyl acetate, 0.61 ml (0.71 g, 5 mmol) of boron trifluoride-diethyl ether complex, 100 ml of dichloromethane, anhydrous.

Procedure: Boron trifluoride etherate was slowly added dropwise at −20° C. to a solution of the acetal in anhydrous dichloromethane. After warming to room temperature, the mixture was stirred for a further 1 h, and the dichloromethane solution was then washed with sodium hydrogen carbonate solution and concentrated. The product mixture was obtained as a viscous oil after chromatography.

Yield: 1.98 g (67%).

Anal. Data: $R_f$ (dichloromethane/methanol 97:3) α-hydroxy product: 0.42; β-hydroxy product: 0.25; α-and β-methoxy product: about 0.45; starting material: 0.50.

EXAMPLE 26 rel-(4R,5S)-5-(3''-Benzyloxy-4''-methoxyphenyl)-7'-benzyloxy-6'-dimethoxy-1',2',3',4'-tetrahydroisoquinolino)-[1,2-c]-oxazolidin-2-one rel-(4R,5S)-5-(3''-Benzyloxy-4''-methoxy-phenyl)-(7'-benzyloxy-4'-hydroxy-6'-methoxy-1',2',3',4'-tetrahydroisoquinolino)-[1,2-c]-oxazolidin-2-one Mixture: 3.5 g (5.7 mmol) of rel-(4R,5S)-4,5-bis(3'-benzyloxy-4'-methoxyphenyl)-3-(2',2'-dimethoxyethyl)-oxazolidin-2-one, 100 ml of acetone, 66.7 ml of concentrated hydrochloric acid Procedure: Concentrated hydrochloric acid was carefully added dropwise at −20° C. under a protective gas atmosphere ($T^{max}=40°$ C.) to the acetal, dissolved in acetone. The reaction mixture was stirred at room temperature for 5 h. Working-up was carried out by addition of dichloromethane, neutralization with concentrated ammonia solution with ice-cooling and subsequent addition of saturated sodium hydrogen carbonate solution. The organic phase was extracted by shaking twice more with sodium hydrogen carbonate solution and concentrated in a rotary evaporator. The product mixture can be purified by chromatography (dichloromethane/methanol 97:3).

Yield: 2.26 g (68%).

Anal. Data: $R_f$(product mixture; dichloromethane/methanol 97:3)=0.51–0.2, $R_f$(starting material)=0.70.

EXAMPLE 27 rel-(αS,1'R) α-(2'-Acetyl-7'-benzyloxy-4'-hydroxy-6'-methoxy-1',2',3',4'-tetrahydroisoquinolinyl)-3-benzyloxy-4-methoxybenzyl acetate Mixture: 3.68 g (5.6 mmol) of rel-(1'S,2'R) bis(3''-benzyloxy-4''-methoxyphenyl)-2'-(acetyl-(2''',2'''-dimethoxyethyl)amino)ethyl acetate, 100 ml of tetrahydrofuran, 66.7 ml of concentrated hydrochloric acid Procedure: Concentrated hydrochloric acid was slowly added dropwise at −10° C. under a protective gas atmosphere to the aminoacetal, dissolved in tetrahydrofuran. The cooling was removed and the mixture was then stirred for about a further 2.5 h at room temperature. The reaction was monitored by thin-layer chromatography. Immediately after reaction of the acetal was complete, dichloromethane was added, the mixture was neutralized with concentrated ammonia with ice-cooling, then sodium hydrogen carbonate solution was added, and the mixture was washed twice more with saturated aqueous sodium hydrogen carbonate solution. The organic phase was concentrated in a rotary evaporator, and the product (atropisomers!) was purified by chromatography (dichloromethane/methanol 99:1).

Yield: 2.15 g (66%).

Anal. Data: $R_f$ (dichloromethane/methanol)=0.56; $R_f$(starting material)=0.46.

EXAMPLE 28 rel-(αS,1'R) α-(7'-Benzyloxy-4'-hydroxy-6'-methoxy-1',2',3',4'-tetrahydroisoquinolin-1'-yl)-3-benzoloxy-4-methoxybenzyl benzoate Mixture: 10.4 g 15 mmol) of rel-(1'S,2'R) bis(3''-benzyloxy-4''-methoxyphenyl)-2'-((2'''-dimethoxyethyl)-methylamino)ethyl benzoate, 446 ml of acetone, 297 ml of concentrated hydrochloric acid.

Procedure: Concentrated hydrochloric acid was carefully added dropwise at −20° C. under a protective gas atmosphere ($T^{max}=40°$ C.) to the acetal, dissolved in acetone. The reaction mixture was stirred at room temperature for 5 h. Working-up was carried out by addition of dichloromethane, neutralization with concentrated ammonia solution with ice-cooling and subsequent addition of saturated sodium hydrogen carbonate solution. The organic phase was extracted by shaking twice more with sodium hydrogen carbonate solution and concentrated in a rotary evaporator. The product mixture can be purified by chromatography (dichloromethane/methanol 99:1)

Yield: 5.4 g (55.6%).

Anal. Data: $R_f$ (dichloromethane/methanol 98:2)=0.43 (β-isomer); 0.28 (α-isomer); 0.72 (starting material).

EXAMPLE 29 rel-(αS,1'R,4'S)-3-Benzyloxy-4-methoxy-α-(7'-benzyloxy-4'-hydroxy-6'-methoxy-1',2',3',4'-tetrahydroisoquinolin-1'-yl)benzyl alcohol Mixture: 10.0 g (15.9 mmol) of rel-(1'S,2'R) 1',2'-bis(-3''-benzyloxy-4''-methoxyphenyl)-2'-(2'''-dimethoxyethylmethylamino)ethyl acetate, 400 ml of acetone, 267 ml of concentrated hydrochloric acid.

Procedure: Concentrated hydrochloric acid was carefully added dropwise at −20° C. under a protective gas atmosphere ($T^{max}=40°$ C.) to the acetal, dissolved in acetone. The reaction mixture was stirred at room temperature for 6 h. Working-up was carried out by addition of some acetone and 50 percent strength NaOH to pH=12. The reaction temperature rose to 60° C. during the course of this. The mixture was subsequently stirred at this temperature for one hour; then the volume was concentrated to one third. After addition of dichloromethane, the mixture was neutralized with concentrated hydrochloric acid; then sodium hydrogen carbonate solution was added, and the mixture was extracted three times with dichloromethane, concentrated in a rotary evaporator and chromatographed.

Yield: 5.26 g (61%).

Anal. Data: $R_f$ (dichloromethane/methanol 95:5)=0.21; $R_f$(starting material)=0.90.

EXAMPLE 30

(2'-Acetyl-6',7'-dimethoxy-1',2'-dihydroisoquinolin-1'-yl)methyl acetate

Mixture: 500 mg (1.35 mmol) of 2'-(3'',4''-dimethoxyphenyl)-2'-(acetyl-(2'''-dimethoxyethyl)-amino)ethyl acetate, 10 ml of acetone, 5 ml of concentrated hydrochloric acid.

Procedure: Concentrated hydrochloric acid was slowly added dropwise at 0° C. under a protective gas atmosphere to the acylated aminoacetal, dissolved in acetone. The cooling was removed, then the mixture was stirred at room temperature for a further 2 h. The reaction was monitored by thin-layered chromatography during the course of this. Immediately after reaction of the acetal was complete, dichloromethane was added, the mixture was neutralized with concentrated ammonia with ice-cooling and then sodium hydrogen carbonate solution was added. After phase separation, the organic phase was washed twice more with saturated, aqueous sodium hydrogen carbonate solution. It was concentrated in a rotary evaporator, and the product was purified by chromatography (dichloromethane/methanol 95:5).

Yield: 220 mg (54%).

Anal Data: $R_f$ (dichloromethane/methanol 9:1)=0.28; $R_f$(starting material)=0.40 atropisomers!

Reductions With Complex Hydrides:

EXAMPLE 31

7-Benzyloxy-6-methoxy-1-(3'-Benzyloxy-4'-methoxybenzyl)-2-methyl-1,2,3,4-tetrahydroisoquinoline Mixture: 3.0 g (5.54 mmol) of rel-(αS,1'R,4'S)-3-benzyloxy-4-methoxy-α-(7'-benzyloxy-4'-hydroxy-6'-methoxy-1'-1',2',3',4-tetrahydroisoquinolin-1'-yl)benzyl alcohol, 150 ml of tetrahydrofuran, abs., 1.13 ml (15.5 mmol) of thionyl chloride, 1.31 ml (15 mmol) of pyridine, 1.57 g (41.4 mmol) of lithium aluminum hydride.

Procedure: Thionyl chloride was added dropwise at 0° C. under a protective gas atmosphere to the dihydroxy compound, dissolved in tetrahydrofuran/pyridine. After 30 min at 0° C., the cooling was removed, and the mixture was slowly warmed to room temperature. The suspension formed in the course of this was stirred for 2 h and cooled again to −20° C. Lithium aluminum hydride was added to the reaction mixture by spatula, the temperature rising to at most 15° C. The cooling was removed, and the mixture was stirred for a further 2 h. For working-up, 1.2 ml of water, 1.2 ml of 15 percent strength NaOH and a further 3.6 ml of water were cautiously added. The resulting residue was filtered off and liberally washed with hot THF. The filtrate was concentrated in a rotary evaporator and chromatographed (dichloromethane/methanol 98:2).

Yield: 1.80 g (64%).

Anal. Data: $R_f$ (dichloromethane/methanol 95:5)=0.42; $R_f$=0.40.

EXAMPLE 32 rel-(αS,1'R) α-(7'-Benzyloxy-6'-methoxy-1',2',3',4'tetrahydroisoquinolin-1'-yl)-3-benzyloxy-4-methoxybenzyl acetate Mixture: 500 mg (0.86 mmol) of rel-(αS,1'R) α-(1',2',3',4'-tetrahydro-7'-benzyloxy-4'-hydroxy-6'-methoxy-1'-isoquinolinyl)-3-benzyloxy-4-methoxybenzyl acetate, 80 mg (1.03 mmol) of pyridine, 110 mg (0.95 mmol) of thionyl chloride, 15 ml of tetrahydrofuran.

Procedure: Pyridine and thionyl chloride were added dropwise at −20° C. to the solution of the starting compound in tetrahydrofuran. After warming to room temperature, the mixture was stirred for a further 30 min and cooled to 0° C. Sodium borohydride, dissolved in tetrahydrofuran, was then added dropwise, and the mixture was stirred for a further 1 h. For working-up, the solvent was concentrated up to 4/5 in a rotary evaporator, and the mixture was then extracted by shaking with dichloromethane/saturated sodium hydrogen carbonate solution. The organic phase was concentrated in a rotary evaporator and chromatographed (dichloromethane/methanol 97:3)

Yield: 0.30 g (62%).

Anal. Data: $R_f$ (dichloromethane/methanol 95:5)=0.49; $R_f$(starting material)=0.36.

Catalytic Hydrogenations:

EXAMPLE 33

2-Acetyl-7-hydroxy-6-methoxy-(3'-hydroxy-4'-methoxybenzyl)-1,2,3,4-tetrahydroisoquinoline (N-acetylnorreticuline)

Mixture: 250 mg (0.42 mmol) of rel-(αS,1'R) α-(2'-acetyl-7'-benzyloxy-6'-methoxy-1',2'-dihydroisoquinolin-1'-yl)-3-benzyloxy-4-methoxybenzyl acetate, 21 ml of ethanol, 14 ml of distilled water, 250 mg of 10 percent palladium on active carbon Procedure: The starting compound was hydrogenated with vigorous stirring at 100° C., and a hydrogen pressure of 85 bar for 18 h in a VA stirring autoclave. Working-up was carried out by filtering off the catalyst, concentrating the filtrate in a rotary evaporator and extracting the product mixture by shaking with dichloromethane/saturated sodium hydrogen carbonate solution. The organic phase was concentrated in a rotary evaporator and chromatographed (dichloromethane/methanol 97:3)

Yield: 90 mg (51.4%).

Anal. Data: $R_f$ (dichloromethane/methanol 95:5)=0.35; $R_f$(starting material)=0.48.

EXAMPLE 34 rel-(αS,1'R) α-(2'-Benzoyl-7'-hydroxy-6'-methoxy-1',2',3',4-tetrahydroisoqunolin-1'-yl)-3-hydroxy-4-methoxybenzyl benzoate Mixture: 1.43 g (2.0 mmol) of rel-(αS,1'R) α-(7'-benzyloxy-6'-methoxy-1 ,2'-dihydroisoquinolin-1'-yl)-3-benzyloxy-4-methoxybenzyl benzoate, 180 ml of isopropanol, 120 ml of distilled water, 1.16 g of 10 percent palladium on active carbon, 1.51 g (16.7 mmol) of oxalic acid.

Procedure: The starting compound was hydrogenated in a rocking autoclave at 65° C. and a hydrogen pressure of 150 bar for 18 h, with vigorous rocking. Working-up was carried out by filtering off the catalyst, concentrating the filtrate in a rotary evaporator and extracting the product mixture by shaking with dichloromethane/saturated sodium hydrogen carbonate solution. The organic phase was concentrated in a rotary evaporator and chromatographed (dichloromethane/methanol 97:3).

Yield: 0.81 g (75.3%).

Anal. Data: $R_f$ (dichloromethane/methanol 95:5)=0.55; $R_f$=0.95.

EXAMPLE 35

2-Benzoyl-7-hydroxy-6-methoxy-(3'-hydroxy-4'-methoxybenzyl)-1,2,3,4-tetrahydroisoquinoline (N-benzoylnorreticuline)

Mixture: 100 mg (0.93 mmol) of rel-(αS,1'R) α-(2'-benzoyl-7'-hydroxyoxy-6'-methoxy-1',2',3',4'-tetrahydroisoquinolin-1'-yl)-3-hydroxy-4-methoxybenzyl benzoate, 21 ml of isopropanol, 2 ml of distilled water, 12 ml of concentrated hydrochloric acid, 500 mg of 10 percent palladium on active carbon.

Procedure: The starting compound was hydrogenated in an autoclave at 70° C., and a hydrogen pressure of 85 bar for 18 h with vigorous rocking. Working-up was carried out by filtering off the catalyst, concentrating the filtrate in a rotary evaporator and extracting the product mixture by shaking with dichloromethane/saturated sodium hydrogen carbonate solution. The organic phase was concentrated in a rotary evaporator and chromatographed (dichloromethane/methanol 95:5).

Yield: 115 mg (48.9%).

Anal. Data: $R_f$ (dichloromethane/methanol 95:5)=0.41; $R_f$(starting material)=0.44.

EXAMPLE 36(A)

7-Hydroxy-(3'-hydroxy-4'-methoxybenzyl)-6-methoxy-2-methyl-1,2,3,4-tetrahydroisoquinoline (reticuline)

Mixture: 2.32 g (3.71 mmol) of rel-($\alpha$S,1'R) $\alpha$-(4'-acetoxy-7'-benzyloxy-6'-methoxy-1',2',3',4'-tetrahydroisoquinolin-1'-yl)-3-benzyloxy-4-methoxybenzyl acetate, 140 ml of ethanol, 93 ml of distilled water, 0.66 g of 10 percent palladium on active carbon.

Procedure: The starting compound was hydrogenated in a 500 ml rocking autoclave at 70° C. and a hydrogen pressure of 85 bar for 18 h, with vigorous rocking. Working-up wa carried out by filtering off the catalyst, concentrating the filtrate in a rotary evaporator and extracting the product mixture by shaking several times with dichloromethane/saturated sodium hydrogen carbonate solution. The organic phase was concentrated in a rotary evaporator and chromatographed (dichloromethane/methanol 9:1).

Yield: 1.58 g (88%).

Anal. Data: $R_f$ (dichloromethane/methanol 9:1)=0.07; $R_f$(starting material)=0.90. Purity: 85.15% HPLC.

EXAMPLE 36(B)

1R-7-Hydroxy-(3'-hydroxy-4'-methoxy-benzyl)-6-methoxy-2-methyl-1,2,3,4-tetrahydroisoquinoline (reticuline)

The compound was prepared as described for the racemate. The hydrochloride was obtained by concentrating with ethanolic hydrochloric acid in a rotary evaporator.

R-reticuline·HCl: $[\alpha]_D = -85.3°$ (c=0.82, methanol; ee=92%.

literature value: $[\alpha]_D = -92.7°$ (c=0.82, methanol).

EXAMPLE 37

7-Hydroxy-(3'-hydroxy-4'-methoxybenzyl)-6-methoxy-2-methyl-1,2,3,4-tetrahydroisoquinoline (reticuline)

Mixture: 300 mg (0.5 mmol) of rel-($\alpha$S,1'R) $\alpha$-(4'-hydroxy-7'-benzyloxy-6'-methoxy-1',2',3',4'-tetrahydroisoquinolin-1'-yl)-3-benzyloxy-4-methoxybenzyl acetate, 20 ml of ethanol, 13.7 ml of distilled water, 300 mg of 10 percent palladium on active carbon, 392 mg (4.35 mmol) of oxalic acid.

Procedure: The starting compound was hydrogenated in an autoclave at 70° C., and a hydrogen pressure of 50 bar for 18 h with vigorous rocking. Working-up was carried out by filtering off the catalyst, concentrating the filtrate in a rotary evaporator and extracting the product mixture several times by shaking with dichloromethane/saturated sodium hydrogen carbonate solution. The organic phase was concentrated in a rotary evaporator and chromatographed (dichloromethane/methanol 9:1).

Yield: 150 mg (88.6%).

Anal. Data: $R_f$ (dichloromethane/methanol 9:1)=0.08; $R_f$ (starting material)=0.85. Purity: 79% HPLC.

EXAMPLE 38

6,7-Dimethoxy-(3',4'-dimethoxybenzyl)isoquinoline (papaverine)

Mixture: 200 mg (0.45 mmol) of rel-(4R,5S)-5-(3'',4''-dimethoxyphenyl)-(4'-acetoxy-6',7'-dimethoxy-1',2',3',4'-tetrahydroisoquinolino)-[1,2-c]-oxazolidin-2-one, 5 ml of abs. toluene, 10 mg of p-toluenesulfonic acid.

Procedure: The reaction mixture was heated under reflux for 3 h, and the reaction solution was washed with saturated sodium hydrogen carbonate solution, concentrated and purified by chromatography.

Yield: 120 mg (79%).

Anal. Data: $R_f$ (dichloromethane/methanol 95:5)=0.53; $R_f$(starting material)=0.65.

EXAMPLE 39

6,7-Dimethoxy-1-methylisoquinoline

Mixture: 100 mg (0.33 mmol) of (2'-acetyl-6',7'-dimethoxy-1',2'-dihydroisoquinolin-1'-yl)-methyl acetate, 4 ml of ethanol, 2 ml of concentrated hydrochloric acid.

Procedure: The reaction mixture was heated under reflux for 2 h, cooled and extracted by shaking with dichloromethane and saturated sodium hydrogen carbonate solution. Purification was carried out by chromatography (dichloromethane/methanol 95:5).

Yield: 37 mg (55%).

Anal. Data: $R_f$ (dichloromethane/methanol 9:1)=0.55; $R_f$(starting material)=0.43.

Combined Acylation/Cyclizations:

EXAMPLE 40 rel-($\alpha$S,1'R)
$\alpha$-(2'-Benzoyl-7'-benzyloxy-6'-methoxy-1',2'-dihydroisoquinolin-1'-yl)-3-benzyloxy-4-methoxybenzyl benzoate Mixture: 5.0 g (8.7 mmol) of rel-(1S,2R)-1,2-bis(3'-benzyloxy-4'-methoxyphenyl)-2-((2',2'-dimethoxyethyl)amino)ethanol, 6.08 ml of benzoyl chloride (0.05 mol), 4.25 ml of pyridine (0.05 mol), 20 ml of dichloromethane, abs.

Procedure: The reaction mixture was stirred at RT for 18 h, with exclusion of air. Working-up was carried out by concentrating in a high vacuum at 60° C. in a rotary evaporator, concentrating twice in a rotary evaporator with toluene and dichloromethan . and extracting by shaking with dichloromethane/water. The organic phase was concentrated in a rotary evaporator and allowed to stand in the air overnight. Purification was carried out by chromatography (dichloromethane/methanol 99:1).

Yield: 2 94 g (59%).

Anal. Data: $R_f$ (dichloromethane/methanol 99:1)=0.29; $R_f$(starting material)=0.24 atropisomers!

Aromatizations:

EXAMPLE 41

6,7-Dimethoxy-(3',4'-dimethoxybenzyl) isoquinoline (papaverine)

Mixture: 400 mg (0.35 mmol) of rel-($\alpha$S,1'R,4'S) $\alpha$-(2'-benzoyl-6',7'-dimethoxy-1',2'-dihydroisoquinolin-1'-yl)-3,4-dimethoxybenzyl benzoate, 2.2 g of 85 percent strength potassium hydroxide solution, 0.90 g (18 mmol) of hydrazine hydrate, 50 ml of ethylene glycol.

Procedure: The reaction mixture was heated to 160° C. and stirred at this temperature under a protective gas atmosphere for 90 minutes. For working-up, the mixture was extracted by shaking with water/dichloromethane. Purification was carried out by chromatography.

Yield: 97 mg (82%).

Anal. Data: $R_f$ (dichloromethane/methanol 97:3)=0.34; $R_f$(starting material)=0.65.

EXAMPLE 42

6,7-Dimethoxy-(3',4'-dimethoxybenzyl)isoquinoline (papaverine)

Mixture: 2.30 g (6 mmol) of rel-(4R,5S)-5-(3'',4''-dimethoxyphenyl)-(6',7'-dimethoxy-1',2'-dihydroisoquinolino)-[1,2-c]-oxazolidin-2-one, 50 ml of 6N hydrochloric acid, 10 ml of methanol.

Procedure: The carbamate was heated under reflux for 5 h in a mixture of methanol/aqueous hydrochloric acid. After neutralization with concentrated ammonia, the mixture was extracted with dichloromethane and concentrated in a rotary evaporator.

Yield: 1.79 g (88%).

Anal. Data: $R_f$ (dichloromethane/methanol 95:5)=0.45; $R_f$(starting material)=0.67.

While only a single embodiment of the present invention has been shown and described, it is to be understood that many charges and modifications may be made thereunto, without departing from the spirit and scope of the invention as defined by the appended claims.

What is claimed is:

1. Process for the preparation of 1-alkyl-1,2,3,4-tetrahydroisoquinoline derivatives of the general formula (1)

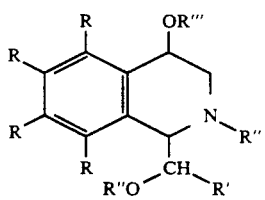

in which

R is H or halogen atoms, alkylamino, dialkylamino, acylamino, hydroxyl, alkoxy, aralkoxy or acyloxy radicals, or in each case, two of the R radicals together form an alkylenedioxy radical;

R' is an H atom or alkyl, acyl or aryl radical or aryl radical substituted by R radicals;

R" is H atoms, acyl, alkyl, aryl or silyl radicals, or two of the R" radicals together, form a diacyl radical;

R'''is H atoms or alkyl radicals comprising the steps of:

(a) reacting compounds of the formulae selected from the group consisting of

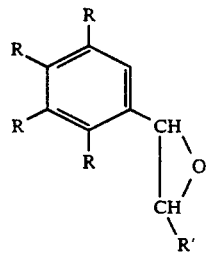

or

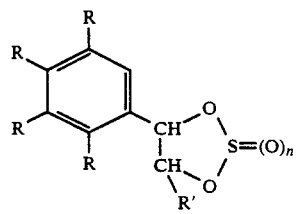

in which R and R' have the above-mentioned meaning, and n=1 or 2, with an amine selected from the group consisting of ammonia, a primary amine and a secondary amine, to cause ring opening, at temperatures in the range of from 50° C. to 200° C. in the presence of protic solvents of Lewis acids to produce a 2-phenyl-2-aminoethanol compound or a 2-phenyl-2-alkylaminoethanol compound;

(b) protecting free OH groups and NH groups in the 2-phenyl-2-aminoethanol compound or the 2-phenyl-alkylaminoethanol compound thus obtained alone or, in each case, together by protective groups selected from alkyl, acyl, silyl, and diacyl radicals; and (c) carrying out ring closure with the formation of the 1-alkyl-1,2,3,4-tetrahydroisoquinoline derivatives (1) via an acetaldehyde or acetaldehyde diacetal group on the nitrogen, at temperatures in the range of from −20° C. to +50° C., in the presence of an aqueous mineral acid or a Lewis acid.

2. Process according to claim 1, comprising:

carrying out the ring opening of the compounds (2) or (3) in process step (a) with ammonia or alkylamine under pressure; and reacting the 2-phenyl-2-aminoethanols or 2-phenyl-2-alkylaminoethanols thus obtained with haloacetaldehydes or haloacetaldehyde dialkyl acetals in the presence of a base, or with ethylene oxide under pressure, and subsequent oxidation of the primary alcohol group to the acetaldehyde group.

3. Process according to claim 1, comprising:

carrying out the ring opening of the compounds (2) or (3) in process step (a) with aminoacetaldehyde dialkyl acetals or alkylaminoacetaldehyde dialkyl acetals in the solvent mixture dichloromethane/isopropanol in the volume ratio 9:1.

4. Process according to claim 1, wherein in the introduction of the protective groups into the compounds (5) in process step (b), the OH and NH groups are either protected alone by reaction with alkyl halide, acyl halide, acyl anhydride or, in each case, together by reaction with oxalyl chloride, dialkyl carbonate or N,N'-carbonyldiimidazole.

5. Process according to claim 1, comprising:
carrying out the isoquinoline ring closure in process step (c) in the presence of an aqueous mineral acid and a water-miscible solvent in the volume ratio 10:90 to 90:10.

6. Process according to claim 1, comprising:
carrying out the isoquinoline ring closure in process step (c) under anhydrous conditions, in the presence of Lewis acids.

7. Process for the preparation of 1-alkyl-1,2,3,4-tetrahydroisoquinoline derivatives of the general formula (1)

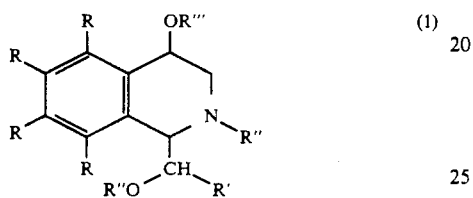

in which

R is H or halogen atoms, alkylamino, dialkylamino, acylamino, hydroxyl, alkoxy, aralkoxy or acyloxy radicals, or in each case, two of the R radicals together form an alkylenedioxy radical;

R' is an H atom or alkyl, acyl or aryl radical or aryl radical substituted by R radicals;

R" is H atoms, acyl, alkyl, aryl or silyl radicals, or two of the R" radicals together, form a diacyl radical;

R'" is H atoms or alkyl radicals comprising the steps of:

(a) reacting compounds of the formulae selected from the group consisting of

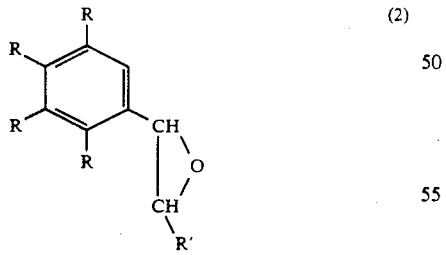

or

-continued

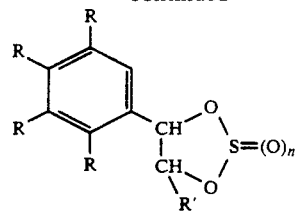

in which R and R' have the above-mentioned meaning, and n=1 or 2, with an amine selected from the group consisting of ammonia, a primary amine and a secondary amine, to cause ring opening, at temperatures in the range of from 50° C. to 200° C., in the presence of protic solvents of Lewis acids to produce a 2-phenyl-2-aminoethanol compound or a 2-phenyl-2-alkylaminoethanol compound;

(b) protecting free OH groups and NH groups in the 2-phenyl-2-aminoethanol compound or the 2-phenylalkylaminoethanol compound thus obtained alone or, in each case, together by protective groups by reaction with alkyl halide, acyl halide, acyl anhydride or, in each case, together by reaction with oxalkyl chloride, dialkyl carbonate or N,N'-carbonyldimidazole; and (c) carrying out ring closure with the formation of the 1-alkyl-1,2,3,4-tetrahydroisoquinoline derivatives (1) via an acetaldehyde or acetaldehyde diacetal group on the nitrogen, at temperatures in the range of from −20° C. to +50° C., in the presence of an aqueous mineral acid or a Lewis acid.

8. Process according to claim 7, comprising:
carrying out the ring opening of the compounds (2) or (3) in process step (a) with ammonia or alkylamine under pressure; and
reacting the 2-phenyl-2-aminoethanols or 2-phenyl-2-alkylaminoethanols thus obtained with haloacetaldehydes or haloacetaldehyde dialkyl acetals in the presence of a base, or with ethylene oxide under pressure, and subsequent oxidation of the primary alcohol group to the acetaldehyde group.

9. Process according to claim 7, comprising:
carrying out the ring opening of compounds (2) or (3) in process step (a) with aminoacetaldehyde dialkyl acetals or alkylaminoacetaldehyde dialkyl acetals in the solvent mixture dichloromethane/isopropanol in the volume ratio 9:1.

10. Process according to claim 7, comprising:
carrying out the isoquinoline ring closure in process step (c) in the presence of said aqueous mineral acid and a water-miscible solvent in the volume ratio 10:90 to 90:10.

11. Process according to claim 7, comprising:
carrying out the isoquinoline ring closure in process step (c) under anhydrous conditions, in the presence of said Lewis acid.

* * * * *